United States Patent
Belden et al.

[11] Patent Number: 5,957,968
[45] Date of Patent: Sep. 28, 1999

[54] SUTURE SLEEVE WITH LEAD LOCKING DEVICE

[75] Inventors: Elisabeth L. Belden; Dale A. Wahlstrom, both of Plymouth; Mark Marshall, Forest Lake, all of Minn.; Scott E. Jahns, Hudson, Wis.

[73] Assignee: Medtronic, Inc., Minneapolis, Minn.

[21] Appl. No.: 08/938,216

[22] Filed: Sep. 26, 1997

[51] Int. Cl.[6] ................................................ A61N 1/05
[52] U.S. Cl. ........................ 607/126; 606/232; 604/175; 607/132
[58] Field of Search ..................... 607/126, 130, 607/132, 115–118; 604/175, 174; 606/138, 139, 228, 232, 213; 24/543, 115 R, 132 R, 132 AA; 248/74.2

[56] References Cited

U.S. PATENT DOCUMENTS

| | | |
|---|---|---|
| 3,176,690 | 4/1965 | H'Doubler . |
| 3,724,467 | 4/1973 | Avery et al. . |
| 3,730,187 | 5/1973 | Reynolds . |
| 3,821,957 | 7/1974 | Riely et al. . |
| 3,880,169 | 4/1975 | Starr et al. . |
| 4,266,552 | 5/1981 | Dutcher et al. . |
| 4,276,882 | 7/1981 | Dickhudt et al. . |
| 4,287,891 | 9/1981 | Peters . |
| 4,516,584 | 5/1985 | Garcia . |
| 4,553,961 | 11/1985 | Pohndorf et al. . |
| 4,672,979 | 6/1987 | Pohndorf . |
| 4,683,895 | 8/1987 | Pohndorf . |
| 4,775,121 | 10/1988 | Carty ............................ 24/543 |
| 5,029,782 | 7/1991 | Andre et al. .................. 248/74.2 |
| 5,107,856 | 4/1992 | Kristiansen et al. . |
| 5,129,405 | 7/1992 | Milijasevic et al. . |
| 5,230,489 | 7/1993 | White et al. .................... 24/543 |
| 5,363,539 | 11/1994 | Tisol ............................. 24/543 |
| 5,683,446 | 11/1997 | Gates ............................ 607/126 |

*Primary Examiner*—Kennedy J. Schaetzle
*Attorney, Agent, or Firm*—Reed A. Duthler; Harold R. Patton

[57] ABSTRACT

An anchoring sleeve for retaining an electrical lead including a sleeve base and a locking member latchable to the sleeve base to lock the locking member to the sleeve base encircling the lead and engaging it around its full circumference. The locking member may be an arcuate member joined to said sleeve base by a hinge and pivotable to latch said locking member to the sleeve base. Alternatively the locking member may be a member formed separately from the sleeve base. The base may be provided with one or more C-shaped members to temporarily retain the lead prior to latching.

6 Claims, 4 Drawing Sheets

SUTURE SLEEVE WITH LEAD LOCKING DEVICE

FIELD OF THE INVENTION

This invention relates to the field of implantable medical devices, and more particularly relates to suture sleeves for implantable leads, catheters, and the like.

BACKGROUND OF THE INVENTION

Implantable leads are used in conjunction with many different types of therapeutic medical devices, such as pacemakers, cardioverters, cardiac defibrillators, neural stimulators, and the like. It is generally deemed desirable to secure an implantable lead in some manner so that proper positioning and placement of the lead is not disturbed. In the past, various techniques and mechanisms have been proposed for securing implanted or partially implanted leads in a patient. When transvenous leads were first introduced in the 1970's, physicians often employed a "butterfly" type anchoring sleeve provided with the lead. The anchoring sleeve, attached to the lead body during implantation, provided a structure adapted to be sutured to a vein or underlying tissue, and further protected the lead insulation from the stress of having a suture tied around it. When polyurethane leads were introduced in the late 1970's, they were frequently provided with a pre-fitted sleeve to facilitate the securing the lead with sutures. Such sleeves were particularly advantageous for polyurethane leads, which tended to have thinner insulation layers than earlier leads. The sleeves were typically silicone rubber, and adapted to slide along the lead body. In operation, the physician would slide the sleeve to a position near where the lead enters the vein, and suture the sleeve to the vein or to underlying tissue to secure the lead.

Several examples of prior art suture sleeves are known in the prior art, including those disclosed in U.S. Pat. No. 4,516,584 issued on May 14, 1985 to Garcia entitled "Suture Collar" (cylindrical collar with longitudinal bore); U.S. Pat. No. 4,553,961 issued on Nov. 19, 1985 to Pohndorf et al. entitled "Suture Sleeve with Structure for Enhancing Pacing Lead Gripping" (cylindrical collar with longitudinal bore containing structure for enhancing gripping between collar and lead); U.S. Pat. No. 4,672,979 issued on Jun. 16, 1987 to Pohndorf entitled "Suture Sleeve Assembly" (tubular sleeve and collet member adapted to snap together); U.S. Pat. No. 4,683,895 issued on Aug. 4, 1987 to Pohndorf entitled "Suture Sleeve Anchoring Device" (circular staple-like clip for attaching a suture sleeve to tissue); U.S. Pat. No. 5,107,856 issued on Apr. 28, 1992 to Kristiansen et al. entitled "Multiple Lead Suture Sleeve" (generally "W"-shaped sleeve adapted to be compressed by sutures around one or two leads); and U.S. Pat. No. 5,129,405 issued to Milijasevic et al. on Jul. 14,1992 entitled "Vein Suture Collar" (cylindrical collar with longitudinal bore).

Other tubular member securing mechanisms have been proposed in the prior art. Earlier examples include U.S. Pat. No. 3,176,690 issued on Apr. 6, 1965 to H'Doubler entitled "Catheter Having Integral, Polymeric Flanges" (elongated external flange integrally formed in the catheter body); U.S. Pat. No. 3,730,187 issued on May 1,1973 to Reynolds (securing collar permanently located on the outer surface of the catheter and having a Dacron polyester suture embedded therein); and U.S. Pat. No. 3,724,467 issued on Apr. 3, 1973 to Avery et al. entitled "Electrode Implant for the Neuro-Stimulation of the Spinal Cord" (physiologically inert plastic tie-down clamp); which described various types of collars or tabs attached to the tubular member for providing a suturing structure.

Still other types of lead or catheter securing devices are disclosed, for example, in U.S. Pat. No. 3,821,957 issued on Jul. 2, 1974 to Riley et al. entitled "Retention Slide for Catheters and Other Tubular Materials" (retention slide having tubular portion and four flexible, radially projecting tabs); U.S. Pat. No. 3,880,169 to Starr et al. on Apr. 29, 1975 entitled "Controlled Entry Pacemaker Electrode for Myocardial Implantation" (rectangular sewing pad adhesively bonded near distal end of lead and providing wings for suturing); U.S. Pat. No. 4,266,552 issued to Dutcher et al. on May 12, 1981 to Dutcher et al. entitled "Lead Anchoring Bobbin" (silicone rubber bobbin for receiving a looped portion of the lead); U.S. Pat. No. 4,276,882 issued on Jul. 7, 1981 to Dickhudt et al. entitled "Lead Anchoring Device" (two-piece disc-shaped device for clamping one or more leads there between); and U.S. Pat. No. 4,287,891 issued on Sep. 8, 1981 to Peters en-titled "Securing Device" (two-piece cylindrical device with longitudinal bore which grips tubular member when twisted).

Known silicone rubber suture sleeves have several disadvantages. Sleeves which must be placed on the lead during manufacture can only be removed by cutting them off, as with a scalpel, when physicians do not wish to use them. This is considered undesirable, since there is a risk that the insulation of the lead would be damaged while the sleeve was being cut off. Moreover, when a silicone rubber suture sleeve becomes wet or infiltrated by moisture, the friction between the lumen of the sleeve and the lead may be reduced so much that the lead is allowed to slide, and is no longer anchored in place.

SUMMARY OF THE INVENTION

In accordance with the present invention, a suture sleeve is provided which has a manually actuated locking device for securing the sleeve at any desired position along the lead body. The sleeve includes a base which is first sutured or stapled to the patient's body tissue adjacent the site of venous insertion. The lead is then snapped into a temporary retention device located on the base. The temporary locking device may comprise one or more C-shaped members into which the lead body can be snapped to temporarily locate the lead and with the locking mechanism in an unlocked position. The position of the lead can still be freely adjusted at this point, either by sliding the lead relative to the sleeve or more typically by first unsnapping the lead and then moving it relative to the sleeve. After determining the desired position of the lead, and snapping it into the temporary retention device, the physician actuates one or more simple locking devices, causing the lead to be secured to the sleeve at the desired position.

In a first embodiment, the locking mechanisms may each comprise a pivotably mounted arcuate member arranged so that its free end may be pivoted into contact with the base member to thereby form a loop to encircle the lead body. The free ends of the arcuate members are provided with latching mechanisms for securing them to the base and thereby securing the lead to the sleeve. The arcuate members are provided with inner surfaces sized so that when encircling the lead body, and locked to the base, the arcuate members engage the outer surface of the lead body tightly enough to prevent longitudinal movement of the lead body without excessively compressing the lead body. The temporary retention device and the locking devices may be mounted to a longitudinal base member with the temporary retention device located between two locking devices.

In a second embodiment the circumferential locking device may comprise a separately formed locking component having one or more C-shaped members which can be snapped to the lead body adjacent the one or more C-shaped members on the base and arranged so that longitudinal movement of the C-shaped members relative to one another is not possible. Preferably, the base and the locking component are provided with a latching mechanism to lock the base and locking component to one another. More preferably, the C-shaped members on the locking component and/or on the base are provided with latching mechanisms to secure the base and locking members to one another to thereby encircle and secure the lead body.

DETAILED DESCRIPTION OF THE PREFERRED EMBODIMENT

Figure 1:
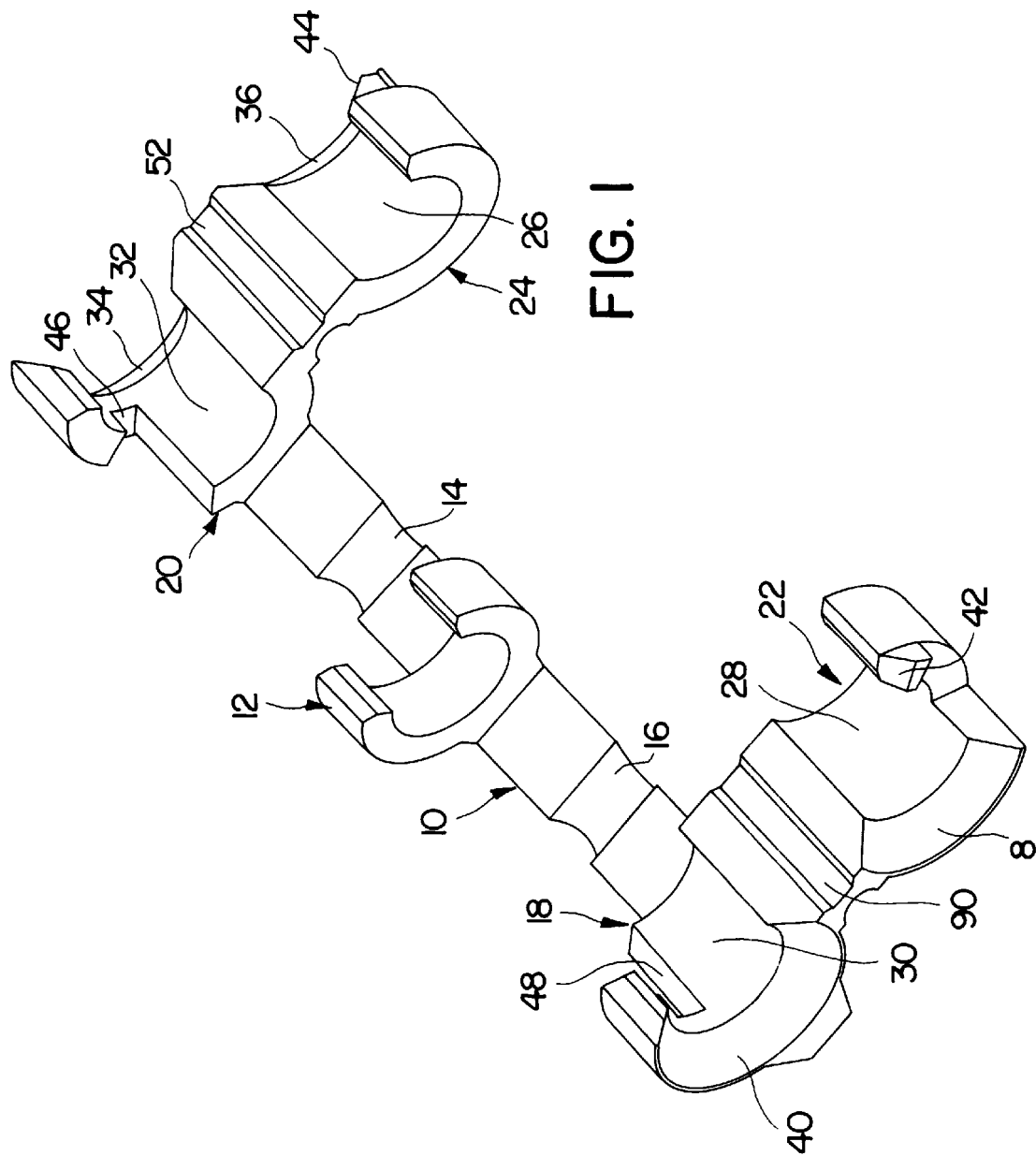
FIG. 1 is a perspective view of an anchoring sleeve according to a first embodiment of the invention.

FIG. 1 is a perspective view of an anchoring sleeve according to a first embodiment of the present invention. This sleeve is fabricated of a flexible biocompatible plastic such as polypropylene or other plastic having a flexural modulus in the range of 150,00–400,00 psi. The sleeve may optionally be coated or overmolded with silicone rubber, polyurethane or other softer biocompatible plastic to reduce tissue iritation and increase the frictional retention force applied to the lead body.

The sleeve includes an elongated base 10, which carries a C-shaped ring 12 which is used to temporarily retain the lead body, as described above. On each end of base 10 are located arcuate members 18 and 20, which together with arcuate members 22 and 24 on base 10 serve to lock the implantable lead to the sleeve. Arcuate members 22 and 24 are coupled to arcuate members 20 and 18 by means of living hinges 52 and 50, respectively. Arcuate members 22 and 24 are provided with latches 42 and 44, respectively and may be pivoted into contact with arcuate members 18 and 20, respectively, so that latches 42 and 44 engage corresponding recesses 48 and 46, respectively. When so engaged, arcuate members 22 and 18 together define an annular structure which is intended to encircle the associated pacing lead, arcuate members 18 and 22 being so sized relative to the lead that when latched, the inner surfaces 30 and 28 frictionally engage the outer surface of the lead body, without unduly compressing it. Similarly, when latched, the inner surfaces 32 and 26 of arcuate members 20 and 24, respectively, also encircle and engage the outer surface of the lead. Preferably, the inner diameter defined by the latched arcuate members should be 3–20% less than the outer diameter of the lead body.

In use, the base 10 is first sutured or stapled to the patient's tissue adjacent the site of venous insertion for the lead by means of staples or suture applied across grooves 14 and 16, molded into the base 10. The elevation of sufraces 30 and 32 and the inner surface of C-shaped member 12 from the upper surface of base 10 assists in maitaining clearance between the staples and the body of the pacing lead. The body of the lead is then snapped into C-shaped member 12, which serves to temporarily retain the lead on the anchoring sleeve. If repositioning of the lead is necessary, the lead may either be slid relative to C-shaped member 12 or the lead body may be snapped out of C-shaped member 12, moved to the desired location, and reinserted into C-shaped member 12. After the lead is located as desired, arcuate members 22 and 24 are pivoted so that latches 42 and 44 engage with corresponding recesses 48 and 46, respectively, encircling the lead and locking it to the anchoring sleeve. The end surfaces, 34, 36, 38 and 40 of arcuate members 20, 24, 18, and 22 are chamfered to provide strain relief at the point at which the lead exits the anchoring sleeve.

Figure 2:
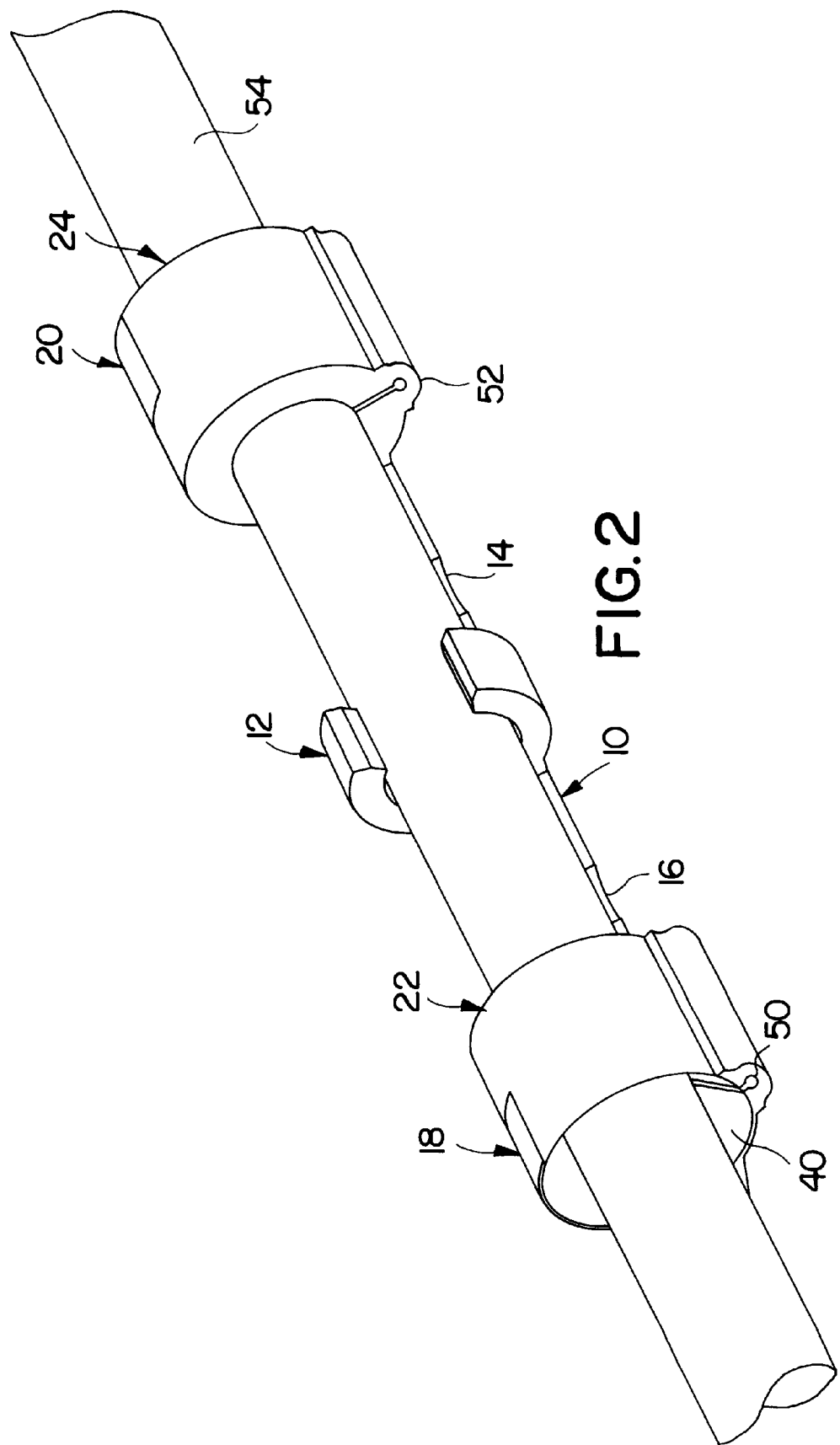
FIG. 2 is a perspective view of the anchoring sleeve of FIG. 1, locked around a lead body.

FIG. 2 illustrates the anchoring sleeve with arcuate members 18 and 22 and arcuate members 20 and 24 latched to one another to encircle the body 54 of an implantable electrical lead. Lead body 54 is shown snapped into C-shaped member 12, which extends around more than half of the circumference of lead body 54. All elements correspond to identically labeled elements in FIG. 1. In this view it can be seen that the pivoting arcuate members 24 and 22 in conjunction with the fixed arcuate members 18 and 20 on base 10 completely encircle the lead, allowing the interior surfaces of the arcuate members to frictionally engage the lead body and prevent longitudinal movement. Engagement of the latches 42 and 44 with corresponding recesses 48 and 46 prevents inadvertent release of the lead from the anchoring sleeve, after implant. However, if it is necessary to replace the lead or reposition the lead after implant, the latches may be unlocked by twisting arcuate members 22 and 24 with a forceps or similar surgical implement, releasing the body 54 of the lead.

Figure 3:
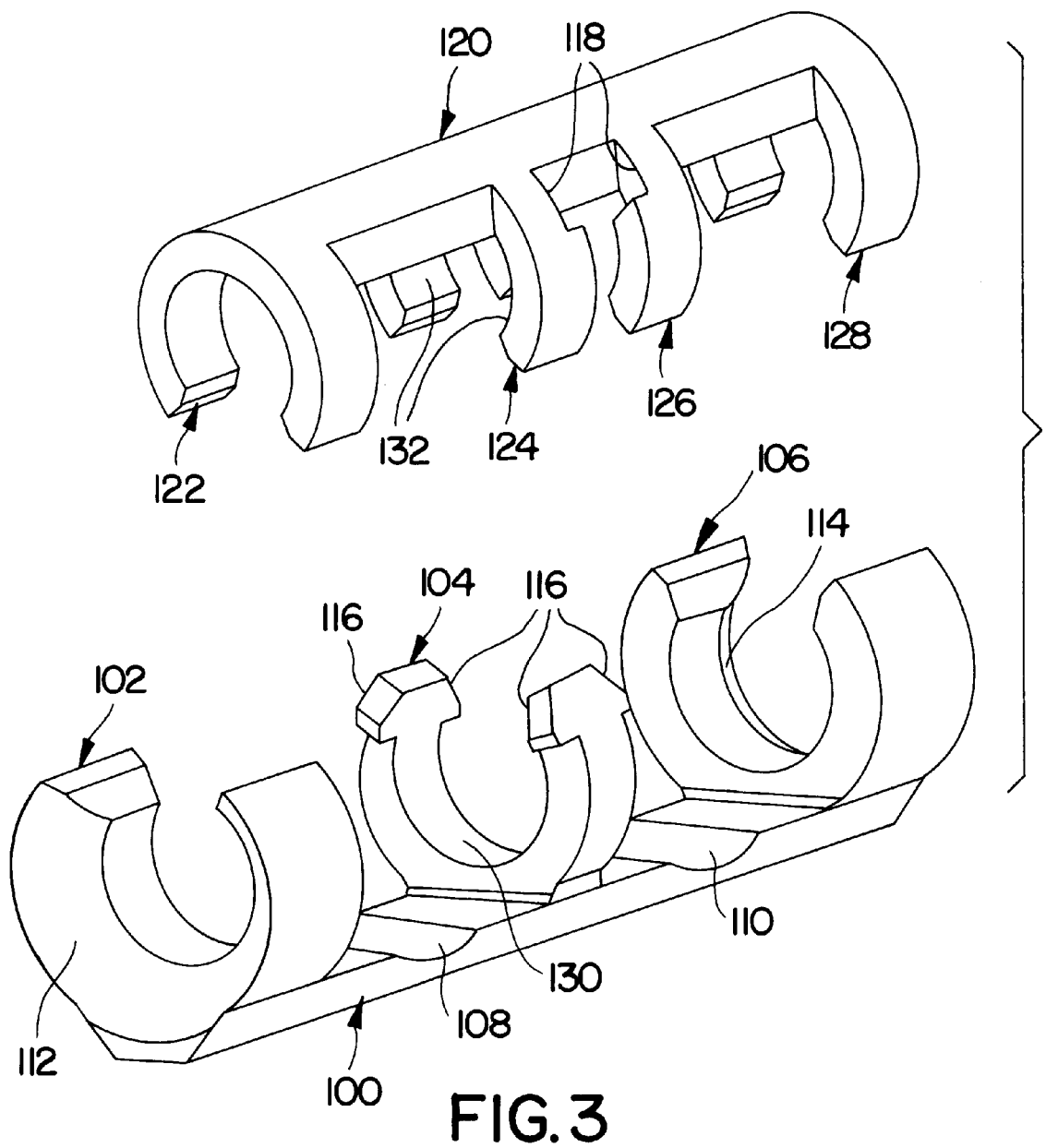
FIG. 3 is a perspective view of an anchoring sleeve according to a second embodiment of the invention.

FIG. 3 is a perspective view of the two components of the second embodiment of an anchoring sleeve according to the present invention. The first component of the sleeve comprises a base 100 which is provided with three C-shaped members 102, 104 and 106. Base 100 is also provided with grooves 108 and 110 which may be employed to staple or suture the base 100 to body tissue, as discussed above, in conjunction with the first embodiment of the invention. Similar to the first embodiment of the invention, C-shaped member 102 and C-shaped member 106 are provided with beveled end surfaces 112 and 114, respectively, which serve as strain release for the exit points of the lead body when engaged with the anchoring sleeve. C-shaped member 104 is provided with latches 116 which serve to retain the locking component 120 of the sleeve to the base 100.

Locking component 120 is provided with four C-shaped members, 122, 124, 126 and 128. C-shaped members 122 and 128 are spaced so that when assembled, they are located inward of C-shaped members 106 and 102 on base 100. C-shaped members 124 and 126 are so located that they will be arranged on either side of C-shaped member 104 of base 100 when the sleeve is assembled. Locking component 120 is also provided with recesses 118 which engage latches 116 in order to secure the locking component 120 to the base 100 after assembly. Base 100 and locking component 120 may be fabricated of a biocompatible plastic such as polypropylene, as discussed above or may be fabricated of harder plastic such as polysulfone. As in the first embodiment, the base and locking member may be coated or overmolded with silicone rubber.

In use, base 100 is first sutured or stapled to body tissue adjacent the site of venous insertion by means of sutures or staples applied across grooves 108 and 110. The lead body is then snapped into C-shaped members 102, 104 and 106.

Subsequently, locking component 120 is snapped onto the lead body with C-shaped members 122 and 128 located inward of C-shaped members 102 and 106, respectively. Latches 116 engage the corresponding recesses 118 on the locking member, securing the locking member to the base 100. The locking member and base are preferably sized so that the inner surfaces 130, 132 of C-shaped members 102, 104, 106, 122, 124, 126 and 128 frictionally engage the lead body without unduly compressing it. Preferably, the inner diameter defined by the C-shaped members should be 3–20% less than the outer diameter of the lead body. Latches 116 and the corresponding recesses prevent inadvertent removal of the lead and locking member 120 from the base 100. If it is necessary to reposition the lead after implant, locking component 120 may be removed from the lead and from base member 100 by means of a forceps or other similar surgical instrument.

Figure 4:
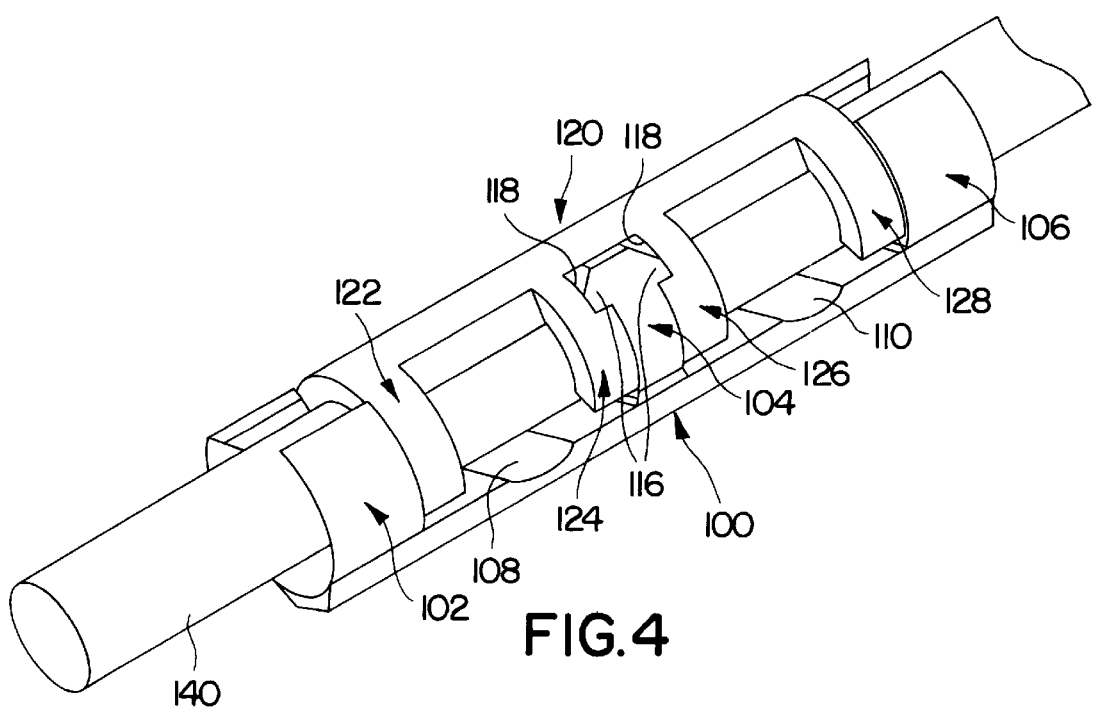
FIG. 4 is a perspective view of the anchoring sleeve of FIG. 3, locked around a lead body.

FIG. 4 illustrates the base 100 and locking component 120 assembled to one another encircling the body 140 of an implantable lead. In this view it can be seen how latches 116 engage in recesses 118 in order to retain the locking component 120 on the base 100. All elements correspond to identically labeled elements in FIG. 3.

While the device illustrated in FIGS. 3 and 4 employs latches located on the central C-shaped member 116 to interconnect the two components of the anchoring sleeve, alternative interconnection mechanisms are possible. For example, one or more of the C-shaped members on the locking component 120 might be provided with notches which engage the edge of base 100 in order to retain the two components in assembled relationship. Alternatively, latches could be provided on any of the other C-shaped members associated with either the base 100 or the locking member 120. It is also possible within the scope of the invention to omit the latching mechanism entirely in this embodiment and simply rely on the snap-fit interconnection of the locking component 120 and the base 100 with the lead body 140 in order to maintain the anchoring sleeve in an assembled configuration. In such an embodiment of the invention, longitudinal movement of the lead relative to the sleeve would be restrained by the frictional interaction of the lead with the base and locking members and by the C-shaped members of the base 100 and locking component 120 with each other.

With regard to the embodiment illustrated in FIG. 1 it should also be understood that while the pivoting arcuate members 22 and 24, as well as the fixed arcuate members 18 and 20, each extend approximately half way around the circumference of the lead to be employed with the sleeve, that other configurations are also possible. For example, the pivoting arcuate members might extend over the substantial majority of the circumference of the body of the lead to be employed with the sleeve, or might extend over substantially less than half of the circumference of the body of the lead to be employed with the sleeve.

As such, the above illustrated first and second embodiments of the invention should be considered exemplary, rather than limiting, with regard to the claims that follow.

We claim:

1. An anchoring sleeve for retaining an electrical lead having a circumference, comprising:

a sleeve base having means for temporarily retaining the lead by engaging the lead around less than its full circumference; and a locking member;

wherein one of said sleeve base and said locking member are provided with a latch and the other of said sleeve base and said locking member are provided with a recess, said latch engageable said recess to lock said locking member to said sleeve base, said sleeve base and said locking member when locked to one another encircling the lead and engaging it around its fall circumference; and wherein said sleeve base and said locking member are fabricated of a first biocompatible plastic coated with a second softer plastic.

2. An anchoring sleeve for retaining an electrical lead having a circumference, comprising:

a sleeve base having means for temporarily retaining the lead by engaging the lead around less than its full circumference;

a locking member; and latching means for locking said locking member to said sleeve base, said sleeve base and said locking member when locked to one another encircling the lead and engaging it around its full circumference;

wherein said locking member comprises an arcuate member joined to said sleeve base by a hinge and pivotable to latch said locking member to said sleeve base; and wherein said sleeve base and said locking member are fabricated of a first biocompatible plastic coated with a second softer plastic.

3. An anchoring sleeve according to claim 1 wherein said locking member is a member formed separately from said sleeve base.

4. An anchoring sleeve according to claim 1 or claim 2 or claim 3 wherein said temporary retaining means comprises at least one C-shaped member on said sleeve base.

5. An anchoring sleeve according to claim 1 or claim 2 or claim 3 wherein said temporary retaining means retains said lead by engaging the lead around more than one half of said lead's full circumference.

6. An anchoring sleeve for retaining an electrical lead having a circumference, comprising:

a sleeve base; and a locking member; and wherein said locking member is provided with means for locking said locking member to said sleeve base, said sleeve base and said locking member when locked to one another encircling the lead and engaging it around its full circumference;

wherein said locking member comprises an arcuate member joined to said sleeve base by a hinge and pivotable to latch said locking member to said sleeve base; and wherein said sleeve base and said locking member are fabricated of a first biocompatible plastic coated with a second softer plastic.

\* \* \* \* \*